United States Patent [19]

Doi et al.

[11] Patent Number: 5,585,253
[45] Date of Patent: Dec. 17, 1996

[54] **EXTRACELLULAR SERINE PROTEASE AND A *BACILLUS SUBTILIS* ALKALINE NEUTRAL AN SERINE PROTEASE MUTANT STRAIN**

[75] Inventors: Roy H. Doi, Davis, Calif.; Lin-Fa Wang, Clayton, Australia; Reinhold Brückner, Ammerbuch, Germany

[73] Assignee: The Regents of the University of California, Oakland, Calif.

[21] Appl. No.: 441,891

[22] Filed: Nov. 27, 1989

[51] Int. Cl.$^6$ ................ C12N 1/21; C12N 9/54; C12N 15/55; C12N 15/75
[52] U.S. Cl. ............... 435/172.3; 435/221; 435/252.31; 435/320.1; 536/23.2; 536/23.7
[58] Field of Search .................. 435/320.1, 252.3, 435/252.5, 172.3, 219, 220, 221, 222, 252.31; 536/27, 23.2, 23.7; 935/14, 29, 56, 72

[56] References Cited

U.S. PATENT DOCUMENTS 4,394,443 7/1983 Weissman et al. .................. 435/6

FOREIGN PATENT DOCUMENTS 2198439 6/1988 United Kingdom .

OTHER PUBLICATIONS

Honjo, M., et al., *J. Biotechnol* (1986) 4:63–71.
Sloma et al. 1988. J. Bacteriol. 170, 5557–5563.
Roitsch et al. 1983. J. Bacteriol. 155, 145–152.
Hunkapiller et al. 1983. Meth. Enzymol. 91, 399–413.
Fahnestock et al 1987. Appl. Environ. Microbiol. 53, 379–384.

*Primary Examiner*—Dian C. Jacobson
*Attorney, Agent, or Firm*—Karen S. Smith; Flehr, Hohbach, Test, Albritton & Herbert

[57] ABSTRACT

A cloned gene (epr) encoding a novel extracellular protease, Epr, from *Bacillus subtilis* is described. Also described is a triple extracellular neutral, alkaline and serine protease deficient *Bacillus subtilis* mutant strain having deletions in the (npr), (apr) and (epr) genes encoding these proteases. The triple mutant strain was constructed by the gene conversion technique and produces about 1% of the extracellular proteolytic activity of the wild type. It is a particularly useful host for the production of heterologous proteins that are secreted into the growth medium.

33 Claims, 11 Drawing Sheets

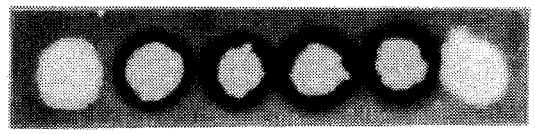
FIG._1B
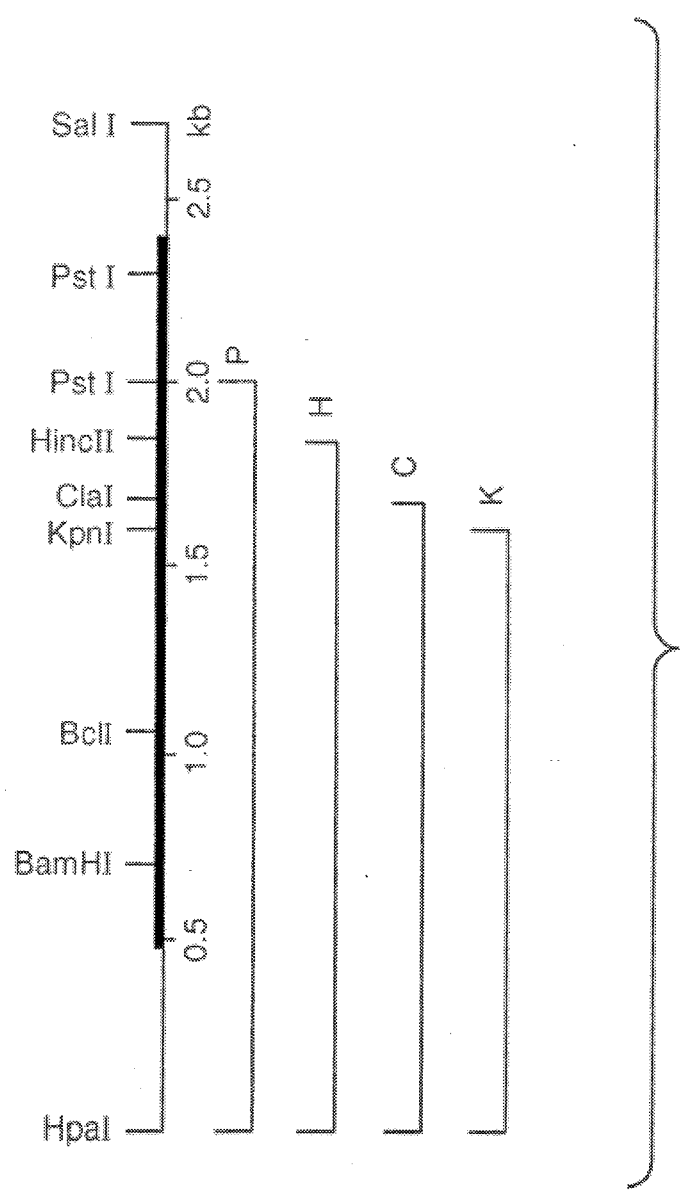
FIG._1A

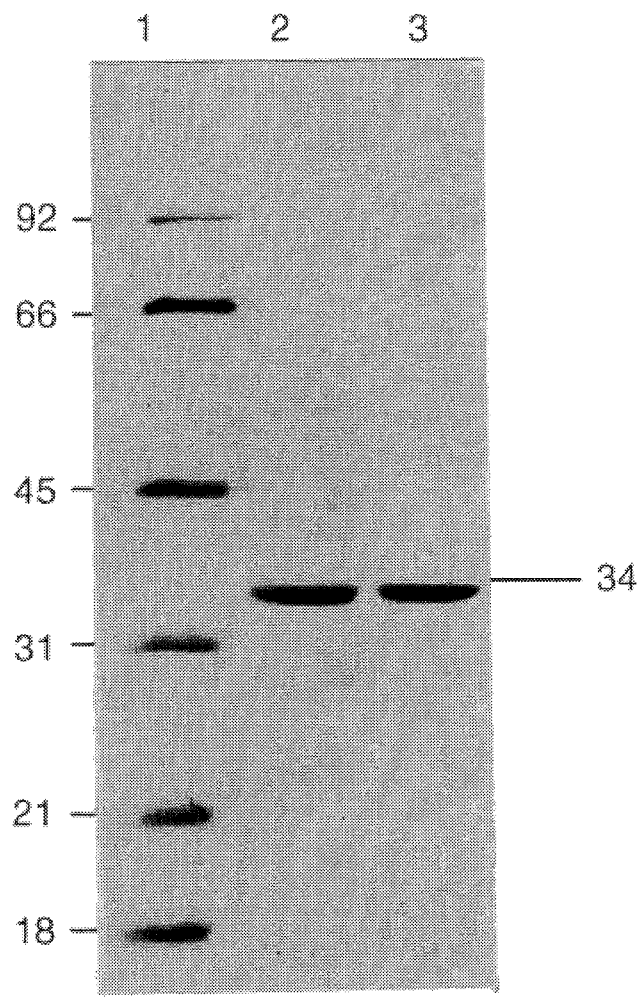
FIG._2

```
HpaI,HincII EcoRV
G TTA AGA GGA TAT CCG AGC TTA TCG GCC CAC TCG TTC CCA AAC ACA CTC GCC ATG AAA TCA   61

GCA TAC CCC GGA ATC GGC AAG CTC GTT AAA ATC AAG AAG ACA GAC CCG ATA ATA ATC AGC  121

GGC ATG GAC TGG ATA ATT CCG TCA CGC AAA GCG CTG AGA TGC CGC TGC CGG GCA ATT TTC  181

CCG GCG ACA GGC ATT ATT TTT TCC TCC ATC ACC CGA GTG AAT GTG CTC ATC TTA AAA ACC  241

CCC TTT TCT CAT TGC TTT GTG AAC AAC CTC CGC AAT GTT TTC TTT ATC TTA TTT TGA  301

AAA CGC TTA GAA ATT CAT TTG GAA AAT TTC CTC TTC ATG CGG AAA AAA TCT GCA TTT TGC  361

TAA ACA ACC CTG CCC ATG AAA ATT TTT TGC TTC TTA CTA TTA ATC TCT CTT TTT TTC TCC  421
```

*FIG._3A*

| *FIG._3A* | *FIG._3B* | *FIG._3C* | *FIG._3D* | *FIG._3E* |

*FIG._3*

```
GAT ATA TAT ATC AAA CAT CAT AGA AAA AGG AGA TGA ATC ATG AAA AAC ATG TCT TGC AAA   481
                                          SD         Met Lys Asn Met Ser Cys Lys   7

CTT GTT GTA TCA GTC ACT CTG TTT TTC AGT TTT CTC ACC ATA GGC CCT CTC GCT CAT GCG   541
Leu Val Val Ser Val Thr Leu Phe Phe Ser Phe Leu Thr Ile Gly Pro Leu Ala His Ala   27

CAA AAC AGC AGC GAG AAA GAG GTT ATT GTG GTT TAT AAA AAC AAG GCC GGA AAG GAA ACC   601
Gln Asn Ser Ser Glu Lys Glu Val Ile Val Val Tyr Lys Asn Lys Ala Gly Lys Glu Thr   47

ATC CTG GAC AGT GAT GCT GTT GAA CAG CAG TAT AAG CAT CTT CCC GCG GTA GCG GTC       661
Ile Leu Asp Ser Asp Ala Val Glu Gln Gln Tyr Lys His Leu Pro Ala Val Ala Val       67
                                                BamHI
ACA GCA CAG GAG ACA GTA AAA GAA TTA AAG CAG GAT CCT GAT ATT TTG TAT GTA GAA       721
Thr Ala Gln Glu Thr Val Lys Glu Leu Lys Gln Asp Pro Asp Ile Leu Tyr Val Glu       87

AAC AAC GTA TCA TTT ACC GCA GCA GAC AGC ACG GAT TTC AAA GTG CTG TCA GAC GGC ACT   781
Asn Asn Val Ser Phe Thr Ala Ala Asp Ser Thr Asp Phe Lys Val Leu Ser Asp Gly Thr   107
                                                                            ***
GAC ACC TCT GAC AAC TTT GAG CAA TGG AAC CTT GAG CCC ATT CAG GTG AAA CAG GCT TGG   841
Asp Thr Ser Asp Asn Phe Glu Gln Trp Asn Leu Glu Pro Ile Gln Val Lys Gln Ala Trp   127

AAG GCA GGA CTG ACA GGA AAA AAT ATC AAA ATT GCC GTC ATT GAC AGC GGG ATC TCC CCC   901
Lys Ala Gly Leu Thr Gly Lys Asn Ile Lys Ile Ala Val Ile Asp Ser Gly Ile Ser Pro   147

CAC GAT GAC CTG TCG ATT GCC GGC GGG TAT TCA GCT GTC AGT TAT ACC TCT TAC AAA       961
His Asp Asp Leu Ser Ile Ala Gly Gly Tyr Ser Ala Val Ser Tyr Thr Ser Tyr Lys       167
```

FIG._3B

```
GAT GAT AAC GGC CAC GGA ACA CAT GTC GCA GGG ATT ATC GGA GCC AAG CAT AAC GGC TAC 1021
Asp Asp Asn Gly His Gly Thr His Val Ala Gly Ile Ile Gly Ala Lys His Asn Gly Tyr  187

BclI
GGA ATT GAC GGC ATC GCA CCG GAA GCA CAA ATA TAC GCG GTT AAA GCG CTT GAT CAG AAC 1081
Gly Ile Asp Gly Ile Ala Pro Glu Ala Gln Ile Tyr Ala Val Lys Ala Leu Asp Gln Asn  207

GGC TCG GGG GAT CTT CAA AGT CTT CTC CAA ATT GAC TGG TCG ATC GCA AAC AGG ATG 1141
Gly Ser Gly Asp Leu Gln Ser Leu Leu Gln Ile Asp Trp Ser Ile Ala Asn Arg Met  227

CAC ATC GTC AAT ATG AGC CTT GGC ACG TCA GAC AGC AAA ATC CTT CAT GAC GCC GTG 1201
Asp Ile Val Asn Met Ser Leu Gly Thr Ser Asp Ser Lys Ile Leu His Asp Ala Val  247

AAC AAA GCA TAT GAA CAA GGT GTT CTG CTT GCC GCA AGC GGT AAC GAC GGA AAC GGC 1261
Asn Lys Ala Tyr Glu Gln Gly Val Leu Leu Ala Ala Ser Gly Asn Asp Gly Asn Gly  267

AAG CCA GTG AAT TAT CCG GCA TAC AGC AGT GTC GTT GCG GTT TCA GCA ACA AAC GAA 1321
Lys Pro Val Asn Tyr Pro Ala Tyr Ser Ser Val Val Ala Val Ser Ala Thr Asn Glu  287

AAG AAT CAG CTT GCC TCC TTT TCA ACA ACT GGA GAT GAA GTT GAA TTT TCA GCA CCG GGG 1381
Lys Asn Gln Leu Ala Ser Phe Ser Thr Thr Gly Asp Glu Val Glu Phe Ser Ala Pro Gly  307

ACA AAC ATC ACA AGC ACT TAC TTA AAC CAG TAT TAT GCA ACG GGA AGC GGA ACA TCC CAA 1441
Thr Asn Ile Thr Ser Thr Tyr Leu Asn Gln Tyr Tyr Ala Thr Gly Ser Gly Thr Ser Gln  327

GCG ACA CCG CAC GCC GCT GCC ATG TTT GCC TTG TTA AAA CAG CGT GAT CCT GCC GAG ACA 1501
Ala Thr Pro His Ala Ala Ala Met Phe Ala Leu Leu Lys Gln Arg Asp Pro Ala Glu Thr  347
```

FIG._3C

```
                                                                                        KpnI
AAC GTC CAG CTT CGC GAG GAA ATG CGG AAA AAC ATC GTT GAT CTT GGT ACC GCA GGC CGC  1561
Asn Val Gln Leu Arg Glu Glu Met Arg Lys Asn Ile Val Asp Leu Gly Thr Ala Gly Arg   367

GAT CAG CAA TTT GGC TAC GGC TTA ATC CAG TAT AAA GCA CAG GCA ACA GAT TCA GCG TAC  1621
Asp Gln Gln Phe Gly Tyr Gly Leu Ile Gln Tyr Lys Ala Gln Ala Thr Asp Ser Ala Tyr   387
                                                                ClaI EcoRV
GCG GCA GAG CAA GCG GTG AAA GCG GAA CAA AAA GCA CAA ACA CAA ATC GAT ATC AAC  1681
Ala Ala Glu Gln Ala Val Lys Ala Glu Gln Lys Ala Gln Thr Gln Ile Asp Ile Asn   407
                                                                       >
                                                                       +++
AAA GCG CGA GAA CTC ATC AGC CAG CTG CCG AAC TCC GAC GCC AAA ACT GCC CTG CAC AAA  1741
Lys Ala Arg Glu Leu Ile Ser Gln Leu Pro Asn Ser Asp Ala Lys Thr Ala Leu His Lys   427

AGA CTG GAT AAA GTA CAG TCA TAC AGA AAT GTA AAA GAT GCG AAA GAC AAA GTC GCA AAG  1801
Arg Leu Asp Lys Val Gln Ser Tyr Arg Asn Val Lys Asp Ala Lys Asp Lys Val Ala Lys   447
                    HincII
CCA GAA AAA TAT AAA ACA CAG CAA ACC GTT GAC ACA GCA CAA ACT GCC ATC AAC AAG CTG  1861
Ala Glu Lys Tyr Lys Thr Gln Gln Thr Val Asp Thr Ala Gln Thr Ala Ile Asn Lys Leu   467
                                            >
CCA AAC GGA ACA GAC GCG AAA AAG AAC CTT CAA AAA CGC TTA GAC CAA GTA AAA CGA TAC ATC  1921
Pro Asn Gly Thr Asp Ala Lys Lys Asn Leu Gln Lys Arg Leu Asp Gln Val Lys Arg Tyr Ile  487

GCG TCA AAG CAA GCG AAA GAC AAA GTT GCG GAA GCG AAA AAG AGC CTG AAA AAG AAA ACA GAT  1981
Ala Ser Lys Gln Ala Lys Asp Lys Val Ala Lys Ala Glu Lys Ser Leu Lys Lys Lys Thr Asp  507
                                                                                PstI
GTG GAC AGC GCA CAA TCA GCA ATT GGC AAG CTG CCT GCA AGT TCA GAA AAA ACG TCC CTG  2041
Val Asp Ser Ala Gln Ser Ala Ile Gly Lys Leu Pro Ala Ser Ser Glu Lys Thr Ser Leu   527
```

FIG._3D

```
CAG AAA CGC CTT AAC AAA GTG AAG AGC ACC AAT TTG AAG ACG GCA CAG CAA TCC GTA TCT 2101
Gln Lys Arg Leu Asn Lys Val Lys Ser Thr Asn Leu Lys Thr Ala Gln Gln Ser Val Ser  547

GCG GCT GAA AAG AAA TCA ACT GAT GCA AAT GCG GCA AAA GCA CAA TCA GCC GTC AAT CAG 2161
Ala Ala Glu Lys Lys Ser Thr Asp Ala Asn Ala Ala Lys Ala Gln Ser Ala Val Asn Gln  567

CTT CAA GGA AAG GAC AAA ACG GCA TTG CAA AAA CGG TTA GAC AAA GTG AAG AAA AAG 2221
Leu Gln Gly Lys Asp Lys Thr Ala Leu Gln Lys Arg Leu Asp Lys Val Lys Lys Lys  587

GTG GCG GCT GAA GCA AAA GTG GAA ACT GCA AAG GCA AAA GTG AAG AAA GCG GAA 2281
Val Ala Ala Glu Ala Lys Val Glu Thr Ala Lys Ala Lys Val Lys Lys Ala Glu  607
                                                                    PstI
AAA GAC AAA ACA AAG AAA TCA AAG ACA TCC GCT CAG TCT GCA GTG AAT CAA TTA AAA GCA 2341
Lys Asp Lys Thr Lys Lys Ser Lys Thr Ser Ala Gln Ser Ala Val Asn Gln Leu Lys Ala  627

TCC AAT GAA AAA ACA AAG CTG CAA AAA CGG CTG AAC GCC GTC AAA CCG AAA AAG TAA CCA 2401
Ser Asn Glu Lys Thr Lys Leu Gln Lys Arg Leu Asn Ala Val Lys Pro Lys Lys ---
                                                                    >
AAA ACC TTT AAG ATT TGC ATT CCA AGT CTT AAA GGT TTT TTT CAT TCT AAG AAC ACC ACA 2461
CAC AAC TTT CTT CCC ATC CAT TGT ACA TGT ACA GGC TTT TCA TAC TAT TGC TAT ACA GCC ATG AAC 2521
```

FIG._3E

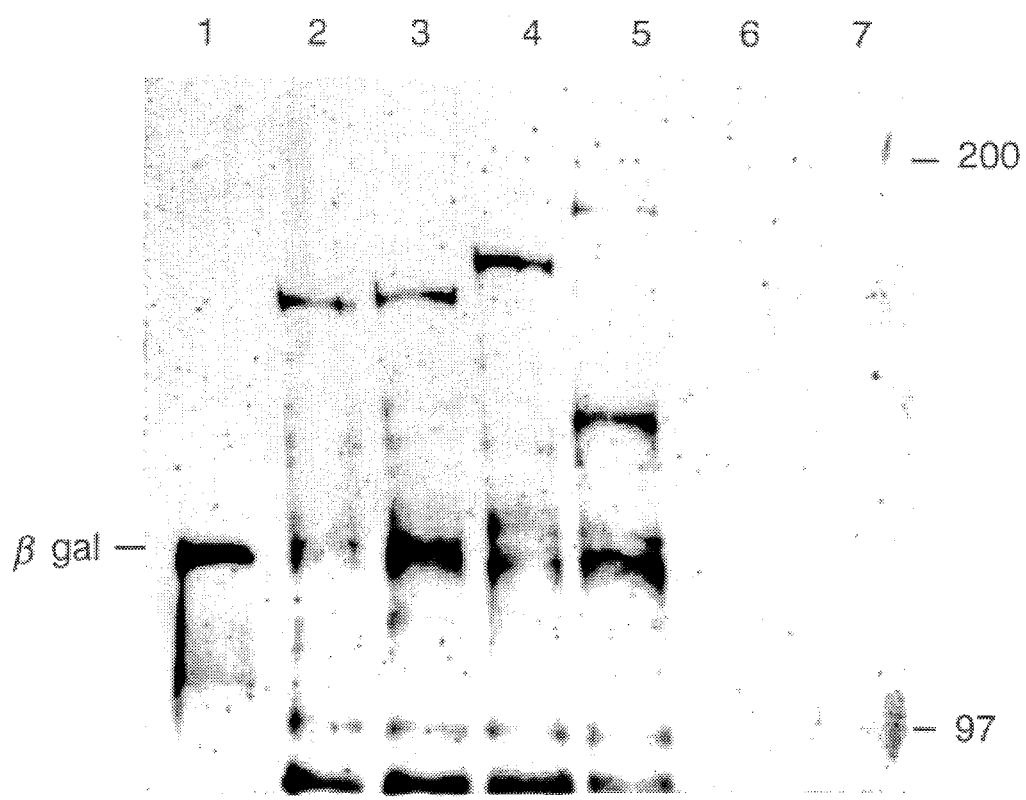
FIG._4

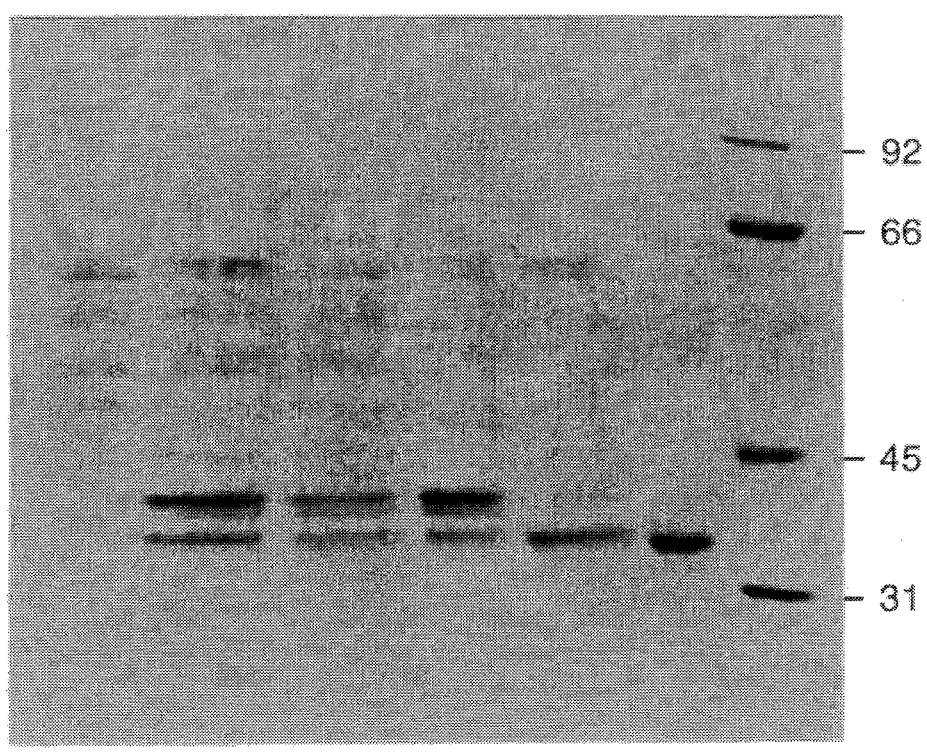
FIG._5
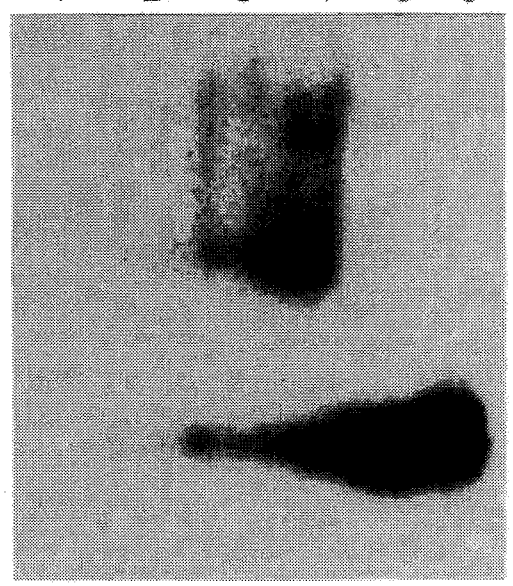
FIG._6

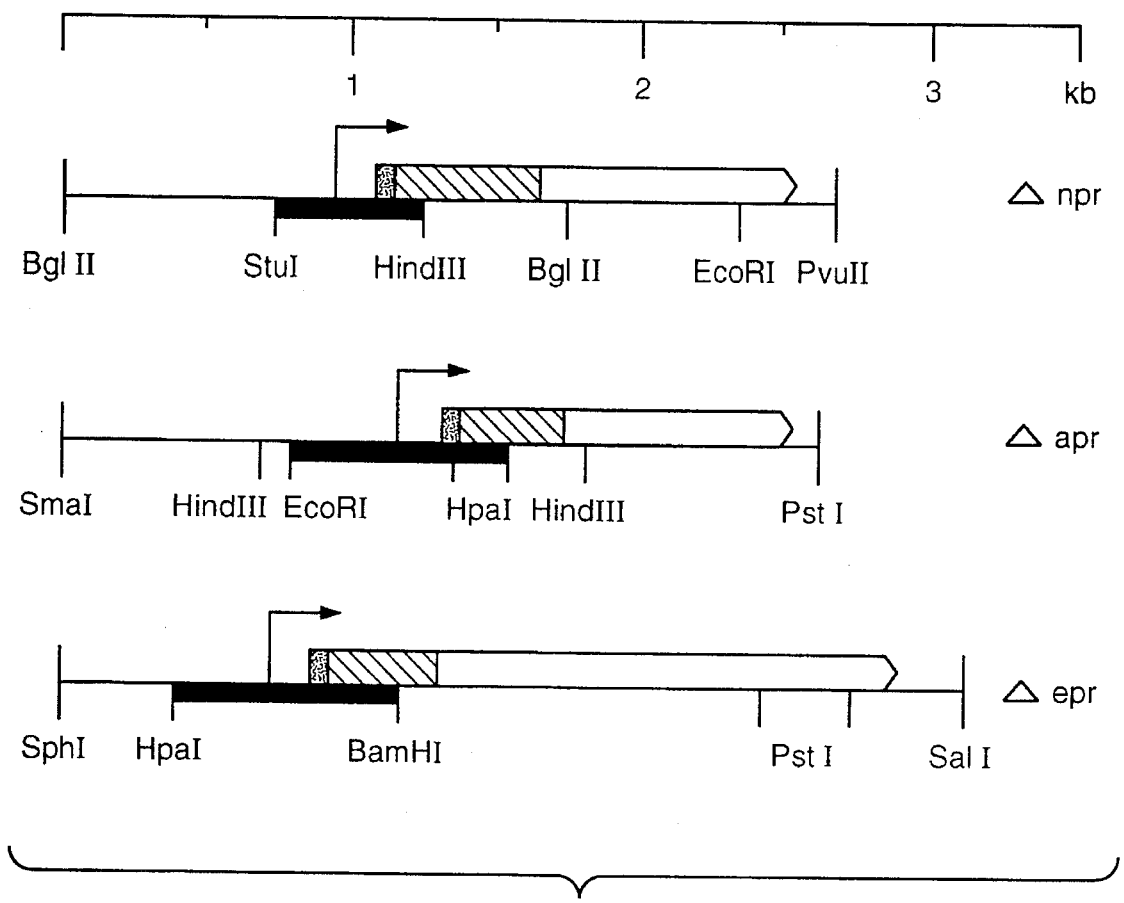
FIG._7

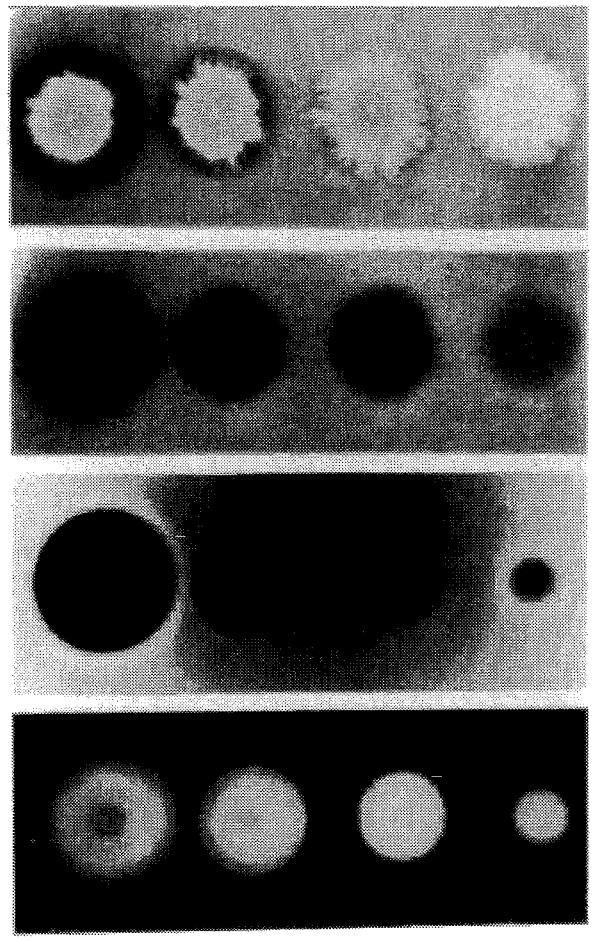
FIG._8

EXTRACELLULAR SERINE PROTEASE AND A BACILLUS SUBTILIS ALKALINE NEUTRAL AN SERINE PROTEASE MUTANT STRAIN

ACKNOWLEDGEMENT OF GOVERNMENT SUPPORT

This invention was made with Government support under Grant Contract No. GM-19673 awarded by the National Institute of Health. The Government has certain rights in this invention.

FIELD OF THE INVENTION

This invention relates to proteases and the development of novel microorganisms. Specifically this invention relates to a novel extracellular serine protease, Epr, the cloning of the gene for that protease, (epr), and a mutant *Bacillus subtilis* strain that has a mutation in that serine protease gene. This invention also relates to a mutant *Bacillus subtilis* strain having deletions for the extracellular neutral protease (nprE) and alkaline protease (aprE) genes as well as the extracellular serine protease (epr) gene. These mutant strains may be used as a host in a recombinant vector-host system where the vector includes genes coding for proteins that are secreted by the host into the growth medium.

BACKGROUND OF THE INVENTION

Recombinant DNA technology has enabled the utilization of microbial organisms for the controlled production of various useful heterologous protein products. Gram positive bacteria, such as *Bacillus subtilis*, are often used as host organisms to produce useful protein products and the bacteria are engineered to extracellularly secrete the heterologous protein products directly into the growth medium. The protein products are then recovered from the growth medium.

During post-exponential growth, wild type *Bacillus subtilis* bacteria secrete, among other enzymes, several lytic proteins called proteases that degrade foreign or heterologous proteins in the growth medium. Due to the action of the proteases, it was often impossible to obtain large quantities of intact heterologous proteins secreted from *B. subtilis*, especially if they are of eukaryotic origin. The inactivation of the major extracellular protease genes encoding neutral (npr) and alkaline protease (apr) reduced the level of extracellular protease activity considerably (See, Kawamura F., and R. H. Doi (1984) "Construction of a *Bacillus Subtilis* double mutant deficient in extracellular alkaline and neutral protease." *J. Bacteriol:* 160: 442–444.), but a residual level was left. Depending on the sensitivity of the proteins to be produced the remaining proteases can still cause degradation. Therefore, the characterization of one of the remaining proteases, in particular purified serine protease, Epr, and isolated DNA sequences encoding such a serine protease would facilitate the construction of a triple extracellular protease, aprE, nprE and epr, deficient *Bacillus subtilis* strain. The use of this strain should increase the yield and stability of secreted heterologous protein products.

SUMMARY OF THE INVENTION

One aspect of the invention is a purified homogeneous serine protease polypeptide. A second aspect of the invention is an isolated DNA sequence encoding a serine protease polypeptide. The DNA sequence encoding the serine protease polypeptide is operably linked to control sequences and is expressed in a culture of a compatible transformed, transfected or infected host. Another aspect is a cloning vehicle containing the DNA sequence. The plasmid, pHC1, containing the HpaI-ClaI fragment of epr and the plasmid pHS1 containing the HpaI-SalI fragment of epr each carried separately in the B. subtilis strain DB801 were deposited with the ATCC, 12301 Parklawn Drive, Rockville, Md. 20852 U.S.A., Sep. 23, 1992. The accession numbers for pHC1 and pHS1 are 75307 and 75306, respectively. The deposits were made in accordance with the 37 C.F.R. 1.801–1.809. Still a further aspect of the invention is a mutant strain of *Bacillus Subtilis* carrying a deletion of the structural gene (epr), including the promoter, signal peptide and part of the pro-region, that codes for extracellular serine protease. Still a further aspect of the invention is a mutant strain of *Bacillus subtilis* having deletions in the structural genes coding for the extracellular neutral protease (nprE) and extracellular alkaline protease (aprE) as well as the extracellular serine protease (epr) gene. This triple protease deficient strain was constructed by introducing defined deletions into the three genes for the extracellular proteases. A deletion in each respective gene was generated in vitro which removed promoter, signal peptide, and part of the pro region. Secondly, the deleted copy of the gene was introduced into the *B. subtilis* genome by gene conversion after transformation with the plasmid carrying the deletion. The triple protease mutant strain produced about 1% of the extracellular proteolytic activity that is found in wild type *Bacillus subtilis* culture supernatants. The *B. subtilis* triple extracellular protease deficient strain DB403 was deposited with the ATCC, 12301 Parklawn Drive, Rockville, Md 20852 U.S.A., Mar. 22, 1993 and has the accession number 55408.

BRIEF DESCRIPTION OF THE DRAWINGS

FIG. 1A is a restriction map of various fragments of the epr gene.

FIG. 1B is a photograph of separate *B. Subtilis* DB801 colonies containing plasmids with the corresponding different epr fragments as shown in FIG. 1A expressing different levels of protease production.

FIG. 2 is a photograph of a Coomassie-blue stained gel showing protease resulting from a purification performed on a Superose 12 column of the eluate from a culture supernatant of DB801 containing the HpaI-ClaI fragment cloned in pHC1.

FIG. 3, composed consecutively of FIGS. 3A, 3B, 3C, 3D and 3E, shows the nucleotide and amino acid sequence of the epr gene.

FIG. 4 represents an immunoblot analysis of epr-lacZ fusion proteins expressed in *B. subtilis*.

FIG. 5 represents a Coomassie-blue stained polyacrylamide gel showing protein expression directed by epr fragments.

FIG. 6 is a photograph of a nitrocellulose blot showing the protease expression directed by the epr fragments of DB801 culture supernatants separated on a 6% non-denaturing polyacrylamide gel.

FIG. 7 represents restriction maps and deletions of the npr, apr, and epr extracellular protease genes.

FIG. 8 is a photograph showing the expression of extracellular protease by colonies of different *B. subtilis* mutants.

Definitions

The small symbol A as used herein indicates a gene deletion.

DETAILED DESCRIPTION OF THE INVENTION

Cloning of the epr gene for a novel extracellular serine protease from B. Subtilis

Materials and Methods

Bacterial strains and plasmids

B. subtilis DB204 (trpC, lys1, phe1, nprR2, nprE18, ΔaprA 3, iSpl::cat) was used for the preparation of chromosomal DNA and for the initial cloning of epr. Subsequently, B. subtilis DB801 (trpC2, apr, npr, ispl::cat) was constructed and used for the epr expression experiments. For mapping epr a cat gene cloned into epr was integrated into DB104 (his, nprR2, nprE18, aprA3, See, Kawamura and Doi, suprA, 1984) which did not, like DB204, contain a cat gene at the ispl locus. Plasmid pRB373 is a derivative of the shuttle plasmid pRB273 (See, Brückner R., E. Zyprian and H. Matzura (1984) "Expression of a chloramphenicol-resistance determinant carried on hybrid plasmids in gram-positive and gram-negative bacteria." *Gene* 32:151–160.) with the pUC18 polylinker region. Plasmid pRB274'lac, described in Brückner R., T. Dick and H. Matzura (1987) "Dependence of expression of an inducible *Staphylococcus aureus* cat gene on the translation of its leader peptide." *Ml, Gen. Genet.* 207: 486–491., used for the construction of the epr-lacZ fusions is also a pRB273 derivative. It contains the truncated 'lacZ gene of E. coli from plasmid pMC1871, (See, Shapira, S. K. et al. (1983), "New versatile plasmid vectors for expression of hybrid proteins coded by a cloned gene fused to lacZ gene sequences encoding enzymatically active carboxy-terminal portion of β-galactosidase, *Gene* 25: 71–82). The strains used for genetic mapping were the reference strains constructed by Dedonder et al. as set forth in "Construction of a kit of reference strains for rapid genetic mapping in *Bacillus subtilis* 168." *Appl. Environ. Microbiol.* 33:989–993 (1977).

DNA manipulation, transformation and transduction

Plasmid DNA isolation and manipulation followed standard procedures (See, generally, Maniatis T., E. F. Fritsch and J. Sambrook, (1982) Molecular cloning: a laboratory manual, Cold Spring Harbor Laboratory Press, New York, N.Y.). Chromosomal *B. Subtilis* DNA was isolated according to J. Marmur (1961), "A procedure for the isolation of deoxyribonucleic acid from microorganisms", *J. Mol. Biol.* 3: 208–218. For the construction of the genomic library 1 μg pRB373 was linearized with BamHI and ligated with approximately 5 μg of SaU3AI fragments of 3–8 kb which had been obtained by partial Sau3AI digestion and purification from agarose gels. The single stranded M13 DNA for sequencing was prepared after cloning restriction and Bal31 generated fragments into M13mp18/19 according to J. Messing (1983) "New M13 vectors for cloning." *Meth. Enzymol.* 101:10–83. DNA sequencing was done by the chain termination method (See Sanger, F. S. Nicklen and A. R. Coulson (1977) "DNA Sequencing with chainterminating inhibitors." *Proc. Nat. Acad. Sci. USA* 74:5463-5467). B. subtilis transformation and phage pBS1 mediated transduction followed published procedures (See, Hoch J. A., Barat M. and C. Anagnostopoulos (1967) "Transformation and transduction in recombination-defective mutants of *Bacillus subtilis*." J Bacteriol. 93: 1925–1937; Contente S. and D. Dubnau (1979) "Characterization of plasmid transformation in *Bacillus subtilis*: Kinetic properties and the effect of DNA conformation." *Mol. Gen. Genet.* 167: 251–258).

Purification of the protease

B. subtilis DB801 harboring pHC1 was grown in LB medium with 5 μg Kanamycin (Km). Two hours after the onset of stationary phase the culture supernatant was collected and precipitated with 70% ammonium sulfate. The precipitated proteins were dissolved in 10 mM Tris-HCl, pH 7.8, 5 mM $CaCl_2$, dialyzed in the same buffer and loaded on a Q-Sepharose column (Pharmacia). Protease containing fractions eluted by a gradient of 0–0.4 M NaCl were pooled, precipitated with 70% ammonium sulfate and separated by FPLC on a Superose 12 column (Pharmacia). The elution buffer was 10 mM Tris-HCl, pH 7.8, 150 mM NaCl, 5 mM $CaCl_2$. Fractions containing the highest protease activity were then precipitated with 90% ethanol at −20° C. Portions were analyzed on SDS polyacrylamide gels (See, Laemmli U.K. (1970) "Cleavage of structural proteins during assembly of the head of bacteriophage T4." *Nature* (London) 227: 680–685) or subjected to automated Edman degradation.

Determination of protease activity

Protease activity was determined using hide powder azure (Sigma) as substrate (See, Wang L. F. and R. H. Doi (1987) "Developmental expression of three proteins from the first gene of the RNA polymerase $\alpha^{43}$ operon of *Bacillus Subtilis*." *J. Bacteriol.* 169: 41904195). The reaction mixture contained 5 mg hide powder, 10 mM Tris-HCl, pH 7.8, 5 mM $CaCl_2$ and 50–500 μl enzyme in a final volume of 1 ml. The assay mix was incubated at 37° C. for 10–30 min. Insoluble hide powder was removed by centrifugation and the absorbance at 595 nm was determined. The influence of inhibitors on activity was either determined by preincubation of the enzyme for 5 min at 37° C. or by the addition of the inhibitor during the assay.

During the protease purification, fractions were screened for activity by spotting 5–20 ul of the fractions on agar plates containing 1% skim milk. The protease activity of halo producing fractions was then determined by the hide powder method. Peptidase activity was measured with succinyl-ala-ala-pro-leu-p-nitroanilide (s-AAPL-pN, Sigma)) and succinyl-ala-ala-pro-leu-p-nitroanilide (s-AAPF-pN, Sigma) as substrates. The reaction mixtures contained 0.1 mM of substrate, 10 mM Tris-HCl, pH 7.8, 5 mM $CaCl_2$ and a suitable amount of enzyme in a final volume of 1 ml. Peptidase activity was monitored by measuring the increase of the absorbance at 410 nm after incubation at 37° C.

Detection of active proteases after polyacrylamide gel electrophoresis

B. subtilis DB801 containing various plasmids were grown in LB medium with 5 μg/ml Km until two hours after the beginning of stationary phase. The culture supernatant was precipitated with 70% ammonium sulfate. Precipitated proteins were dissolved in 10 mM Tris-HCl, pH 7.8, 5 mM $CaCl_2$ and precipitated with 90% ethanol at −20° C. The precipitate was dissolved in 10 mM Tris, pH 7.8, and subjected either to SDS polyacrylamide gel electrophoresis for size determination or to nondenaturing gel electrophoresis (See, Hedrick, J. L. and A. J. Smith (1968) "Size and charge isomer separation and estimation of molecular weights of proteins by disc gel electrophoresis." *ArCh. BioChem, Biophys.* 126:155–164.) for activity staining. Proteins were then blotted to a nitrocellulose membrane. Transfer was done at 4° C. in a Tris-glycine (25 mM, 192 mM, pH 8.3) buffer. After incubation of the membrane at 37° C. for two hours in a solution containing 2 mM s-AAPL-pN, 200 mM Tris-HCl, pH 8.4, 5% dimethylformamide, 0.1% $NaNO_2$ and 0.5% N-alpha-naphthyl-ethylenediamine hydrolysis of the peptide substrate by the protease was visualized by about 10% trichloracetic acid (TCA) precipitation as a purplish precipitate on the membrane.

Western Blotting

B. subtilis DB801 with epr-lacZ fusion plasmids were grown in LB medium with 5 μg/ml Km until two hours after the start of stationary phase. Cell lysis and immunoblotting was performed as described in Wang and Doi, 1987, supra. Primary (rabbit anti-β-galactosidase) and secondary (goat anti-rabbit IgG antibodies, peroxidase conjugated) were purchased from Cappel.

Results

The novel serine protease gene of the triple protease mutant strain DB204, was cloned by isolating the chromosomal DNA and digesting partially with Sau3AI. Fragments of 3–8 kb were isolated and ligated with the shuttle vector pRB373 that had been linearized with BamHI. After transformation of competent DB204 cells, one of 8000 transformants was found to produce a halo on agar plates containing 1% skim milk. The colony contained a plasmid with an insert of 7.5 kb. By subcloning and deletion experiments a 1.6 kb HpaI-ClaI fragment was identified as the smallest fragment directing the expression of the protease (See, FIG. 1A and 1B). FIGS. 1A and 1B show the restriction map Of the epr gene and protease expression directed by corresponding epr fragments. The restriction map of the HpaI-SalI fragment containing the complete gene is shown with restriction sites of interest. The fragments were all cloned in the same orientation in pRB373 by joining HindIII linkers to the HpaI site. The plasmids containing different epr fragments were designated as follows: HpaI-SalI, pHS1; HpaI-PstI, pHP1; HpaI-HinQII, pHH1; HpaI-ClaI, pHC1, HpaI-KpnI, pHK1. FIG. 1B shows protease expression of B. subtilis DB801 harboring the different epr plasmids on Tryptose blood agar base (TBAB) (Trademark for Difco Laboratories, Detroit, Mich.) agar plates containing 1% skim milk and 5 μg/ml Km. The cells were grown for 16 hours at 37° C. The top colony in FIG. 1B (i.e., the control) shows the protease production of DB801 with pRB373. Further deletion of about 100 bp to the KpnI site totally abolished protease production (FIGS. 1A and 1B).

Mapping of the cloned gene

To locate the cloned gene on the B. subtilis chromosome the cat gene of plasmid pUB112, located on a Sau3AI fragment (See, Brückner et al., 1984, supra) was cloned into the unique BCII site inside the HpaI-ClaI fragment on plasmid pHC1 (FIG. 1A.). The resulting plasmid which did not confer protease overproduction any more was linearized and transformed to DB104. Chloramphenicol (Cm) resistant transformants (e.g., DB802) were obtained that were generated by integration of the cat gene at the protease locus by homologous recombination. Compared to the parental strain DB104, the Cm resistant colonies produced a reduced level of extracellular protease activity as estimated by the halo size on skim milk plates. The correct integration was confirmed by Southern blot analysis. The location of the cat gene was determined by phage pBS1 mediated transduction. A 80% cotransduction frequency for the cat gene with sacA321 was obtain, hence the cloned protease gene is tightly linked to sacA.

Characterization of the protease

B. subtilis cells containing the HpaI-ClaI fragment cloned on plasmid pHC1 were then used to purify the protease from the culture medium. After ammonium sulfate precipitation, ion exchange chromatography, and FPLC gel filtration, fractions with high protease activity were collected. They showed a single protein band of 34 kDa on Coomassie-blue stained SDS polyacrylamide gels (See, FIG. 2). FIG. 2 shows an SDS polyacrylamide gel electrophoresis of the purified protease which was purified from the culture supernatant of DB801 containing the HpaI-ClaI fragment cloned in pHC1. Two fractions (lanes 2 and 3) from a Superose 12 column with highest protease activity were separated on a 12% SDS polyacrylamide gel together with standards obtained by Biorad and stained with Coomassie-blue. The molecular masses are indicated in kDa (lane 1). Residues 4–10 of the protease were determined by amino-terminal sequencing, whereas the first three positions were ambiguous. The amino acid sequence from position 4–10 was as follows: Thr, Asp, Thr, Ser, Asp, Asn and Phe, as shown in FIG. 3. FIG. 3 sets forth the nucleotide and deduced amino acid sequence of the epr gene. The Shine-Dalgarno sequence, the amino acids determined by N-terminal sequencing of the purified protease and a putative transcriptional terminator are underlined. The N-terminus of the mature enzyme is indicated by *** and the last amino acid coded on the HpaI-ClaI fragment with +++. The amino acids Asp, His, and Ser, forming the active center are marked with a ●. The position of the epr-lacZ fusion junctions are indicated by a >.

The activity of the enzyme dissolved in Tris-HCl, pH 7.8, could be inhibited by 1 mM phenylmethylsulfonylfluoride (PMSF) and 1 mM EDTA during the protease assay or by preincubation of the enzyme with either of the two chemicals at 37° C. for 5 min. Analysis of the preincubated samples by SDS polyacrylamide gel electrophoresis revealed that no protein band at 34 kDa could be detected by Coomassie-blue staining after EDTA incubation, but the PMSF treated enzyme was still present. The inhibition of the protease activity was therefore due to the degradation of the enzyme. It was probably caused by disruption of its conformational integrity by chelating agents and subsequent autolytic digestion. Even without EDTA the purified enzyme lost its activity rather quickly during incubation at 37° C. This loss could be decreased by the addition of 5 mM $CaCl_2$ but not prevented totally. The new isolated protease of B. subtilis, Epr, is therefore a serine protease that requires $Ca^{2+}$ for stability. Tests with synthetic peptide substrates revealed that the Epr protease could hydrolyse s-AAPL-pN and S-AAPF-pN, substrates that are also cleaved by subtilisin. (See, Wells J. A. and D. A. Estell (1988) "Subtilisin—an enzyme designed to be engineered." TIBS 13: 291–297.)

Nucleotide sequence of the protease gene

Determination of the sequence of the HpaI-ClaI fragment yielded an open reading frame (ORF) starting with ATG at position 461 as shown in FIG. 3. It is preceded by a Shine-Dalgarno sequence which has a calculated binding energy with the 16S B. subtilis rRNA of −16.4 kcal/mol. (See, Tinoco J. Jr., P. N. Borer, B. Dengler, M. D. Levine, O. C. Uhlenbeck, D. M. Crothers and J. Gralla (1973) "Improved estimation of secondary structure in ribonucleic acids." Nature (London) New Biol. 246: 40–41.) The deduced amino acids at nucleotide positions 779–799 (FIG. 3) are identical with amino acids 4–10 at the N-terminus of the purified protease. The ORF coded on the HpaI-ClaI is therefore the structural gene (epr) for the serine protease. Following the ATG a typical signal peptide sequence of 26 amino acids is found with a positively charged N-terminus, a stretch of hydrophobic amino acids and a Ala-X-Ala peptidase cleavage site (See, yon Heijne (1985) "Signal sequences. The limits of variation." J. Mol. Biol. 184: 90–105). Deduced from the N-terminal sequencing of the purified enzyme, the mature protease starts with a Ser at about amino acid position 104 (FIG. 3). Like neutral protease and subtilisin (i.e. the alkaline protease) of *B. subtilis* (See, Yang M. Y., E. Ferrari, and D. J. Kenner (1984) "Cloning of the neutral protease gene of *Bacillus subtilis* and the use of the cloned gene to create an in vitro-derived deletion." *J. Bacteriol.* 160: 15–21.; Wong S. L, C. W. Price, D. S. Goldfarb and R. H. Doi (1984) "The subtilisin E gene of *Bacillus subtilis* is transcribed from a $\sigma^{37}$ promoter in vivo." *Proc. Natl. Acad. Sci. USA* 81: 1184–1188.) this enzyme is also produced as a preproprotein. The pro-part consists of 76 amino acids.

Although a functional enzyme was produced from the HpaI-ClaI fragment, the open reading frame did not stop in front of the ClaI site. The DNA sequence of the ClaI-SalI fragment (FIG. 1A) was then determined and the ORF was found to be terminated beyond the second PstI site (FIGS. 1A and 3) about 700 bp downstream of the ClaI site. Apparently, more than 200 amino acids coded at the 3'-end of the gene are not needed for an active enzyme.

Confirmation of the open reading frame by translational fusions.

To confirm the size of the gene, translational fusions with a truncated lacZ gene of E, coli were constructed. Three restriction sites were used for the fusions: RSaI at position 1549 (FIG. 3), which cuts a subsequence of the KpnI recognition site, EcoRV at 1675 (FIG. 3), which also cuts at position 10, and HincII at 1831 (FIG. 3). The RSaI site is located inside the minimal protease fragment, whereas the other sites are outside. Plasmid pHS1, which contains the HpaI-SalI protease fragment clones (FIG. 1A) as a HindIII-SalI fragment, was cut with the respective enzymes and 10mer XbaI linkers were ligated to the blunt ended sites. HindIII-XbaI fragments (for RsaI and HincII) and a XbaI fragment (for EcoRV) were then cloned into the vector pRB274'lac. Blue *B. subtilis* colonies were obtained on X-gal plates in each cloning. They contained plasmids (placR, placE, placH) with the predicted restriction maps. Because no convenient restriction sites were present at the extreme 3'-end of epr, the exonuclease Bal31 was used to construct a fusion in this region. Starting at the SalI site downstream of the ORF with Bal31 digestion, several blue transformants could be obtained after cloning the Bal31 generated fragments into pRB274'laC. by means of XbaI linkers. The fusion closest to the end of epr (on placB) was chosen for further analysis. All fusion junctions were sequenced. The fusions generated by restriction enzymes and XbaI linkers were as predicted (FIG. 3). The Bal31 fusion on plasmid placB occurred at position 2383 (FIG. 3), four amino acids before the end of the ORF.

In cell extracts of *B. subtilis* containing the four fusion plasmids, Epr-β-Gal fusion proteins were identified by immunoblotting with anti-antiserum and their sizes were determined. In cells harboring plac R, E, H or B fusion, proteins of 158, 162, 168, and 180 kDa were detected (See., FIG. 4; FIG. 4 shows an immunoblot analysis of epr-lacZ fusion proteins expressed in *B. subtilis*. *B. subtilis* cell lysates corresponding to 0.3 ml culture were fractionated on 7.5% polyacrylamide SDS gels and blotted onto a nitrocellulose membrane. β-galactosidase was detected using rabbit-anti-β-galactosidase antiserum and peroxidase linked to goat anti-rabbit IgG antibodies. Lane 1 contained 1 ug β-galactosidase from E. Coli (Biorad). Lanes 2 through 6 contained DB801 cell extract harboring placR (lane 2), place (lane 3), placH (lane 4), placB (lane 5) and pRB274'laC (lane 6). Lane 7 contained prestained molecular mass markers indicated in kDa (BLR)). The values obtained from the immunoblot analysis are well within the range of the predicted molecular masses of 153, 157, 164 and 183 kDa, respectively. The size of the gene is therefore confirmed by these fusions.

Protease expression directed by different fragments

To determine which proteases would be expressed from the full length HpaI-SalI fragment (pHS1) and from two shorter fragments, the HpaI-PstI fragment on plasmid pHP1 and the HpaI-HincII fragment on pHH1, concentrated media from cultures containing plasmids pHS1, pHP1, pHH1 or pHC1 (See, FIG. 1) were analyzed on SDS polyacrylamide gels and compared with the culture supernatant of cells with the vector pRB373 without insert. From pHS1 four proteins of molecular masses of 40, 37, 36 and 34 kDa were produced (See FIG. 5) that were not found in cultures with pRB373. (FIG. 5 shows protein expression directed by epr fragments. One ml aliquots of culture supernatants were concentrated and separated on a 10% SDS polyacrylamide gel and stained with Coomassie-blue. Lanes 1 through 5 contained supernatant of DB801 harboring the following different plasmids: pRB373 without insert (lane 1), pHS1 (lane 2), pHP1 (lane 3), pHH1 (lane 4), and pHC1 (lane 5). Lane 6, protease produced by pHC1. Lane 7, molecular mass markers indicated by kDa (Biorad)). As shown in FIG. 5, the 40 kDa species could not be detected anymore in cultures with plasmids pHP1 and pHH1, whereas the 37, 36 and 34 kDa proteins were still present. In pHC1 supernatants only the 34 kDa protein remained. Because the protease fragments are truncated at the 3'-end of the gene, the size differences of the proteins must be a consequence of variable C-termini.

To determine if these proteins are all active as proteases, activity staining was performed using s-AAPL-pN as substrate. The same culture supernatants as above were separated on non-denaturing polyacrylamide gels and blotted on nitrocellulose membranes. Hydrolysis of the synthetic substrate by the protease was then visualized as a precipitate on the membrane (See, FIG. 6; FIG. 6 also shows protease expression directed by epr fragments. The same culture supernatants as in FIG. 5 were separated on a 6% nondenaturing polyacrylamide gel. After transfer to nitrocellulose, protease activity was detected by hydrolysis of a peptide substrate. Lanes 1 through 5 contained supernatant of a DB801 culture harboring pRB373 without insert (lane 1), pHS1 (lane 2), pHP1 (lane 3), pHH1 (lane 4), and pHC1 (lane 5). Lane 6 contained purified protease produced by pHC1). In lanes with protease preparations from pHS1, pHP1 and pHH1 cultures, three bands appeared. With pHC1 only one could be detected. These activity bands corresponded to the 37, 36 and 34 kDa forms found on SDS gels indicating that these species are active proteases. The activity of the 40 kDa form found exclusively in pHS1 preparations could not be demonstrated by this analysis.

DISCUSSION

In the culture medium of *B. subtilis* cells containing the epr gene cloned on a plasmid, four proteins of 40, 37, 36 and 34 kDa were detected that were expressed from the gene. By activity staining after non-denaturing gel electrophoresis the 37, 36 and 34 kDa forms were found to be active as proteases. Activity of the 40 kDa species could not be demonstrated. After FPLC gel filtration, however, fractions with high protease activity towards casein have been collected that contained the 40 kDa protein almost exclusively. The 40 kDa form, therefore, is also appears active. The amount of this species in the medium was probably not sufficient to give a positive result in the activity staining procedure.

Deletion of 354 bp at the 3'-end of the gene to the PstI site abolished the production of the 40 kDa form. Further deletion of 210 bp to the HincII site did not change the expression pattern. Removal of an additional 154 bp stopped the expression of the 37 and 36 kDa species leaving only the smallest 34 kDa enzyme. Since a change in the expression of the protease species has been achieved by deletions at the 3'-end of epr, the enzymes most likely have a common N-terminus, the same as determined for the 34 kDa protein, and differ in their C-termini. These are generated either by degradation or processing at different positions of the C-terminus.

The deduced size of the mature protease starting with Ser at position 104 (FIG. 3), the N-terminus 34 kDa protease, and ending with the stop codon at amino acid position 646 (FIG. 3), is about 60 kDa. The molecular mass of the largest protein produced by apr was found to be 40 kDa as determined by SDS polyacrylamide gel electrophoresis. The same value has been obtained by FPLC gel filtration. The difference between the calculated and the apparent molecular masses suggests that the 40 kDa protein does not represent the full length translation product of the epr gene after removal of the signal peptide and the pro-part. It seems that the largest form of the protease is already processed at the C-terminus. Additional removal of C-terminal amino acids leads to the 37, 36 and 34 kDa forms.

The minimal sequence for an active enzyme is coded on the HpaI-ClaI fragment (See, FIG. 1). Comparison of the part of Epr coded on that fragment with subtilisin revealed a homology of 40%, which ends about 30 amino acids in front of the HpaI site. Parts of the homologous sequence are deleted on the HpaI-KpnI fragment which did not confer the expression of a functional enzyme. The amino acids found to form the active center of serine proteases, namely Asp, His, and Ser (See, Walsh K. A. 1975 "Unifying concepts among proteases." In: Reich E., D. B. Rifkin and E. Shaw (eds.) Proteases and biological Control. Cold Spring Harbor Laboratory, N.J.), are located at positions 39, 69 and 223 of the mature enzyme (FIG. 3), at positions similar to subtilisin (positions 32, 64 and 221, respectively) (Wells and Estell, 1988, supra).

The comparison with subtilisin confirms that the epr gene is composed of two parts, one coding for a protease and the other coding for a C-terminus of unknown function. The C-terminus is unusually rich in basic amino acids with about 24% Lys. Depending on how many of the C-terminal amino acids were removed, the positive charge at the C-terminus of the different Epr forms could vary considerably. This could play a role in their interaction with protein substrates that are also charged and thus regulate activity towards specific substrates.

The four proteins found in this study probably reflect the fact that non-isogenic strains were used. This would mean that Epr processing might be variable depending on the strain and growth conditions. It is also possible that overproduction of Epr from a multi-copy plasmid changes the processing pattern because the responsible processing enzyme(s) could be limiting.

In conclusion, this serine protease, Epr, from *B. subtilis* that has the potential of C-terminal variation might serve as a regulatory mechanism to moderate protease production and activity, and might allow the cell to accommodate to various environmental conditions and substrates. p Construction of a triple extracellular protease deficient *B. subtilis* strain, DB403

Bacterial strains and plasmids

DB2 (trpC2), DB104 (his, nprR2, nprE18, A aprA3) and DB802 (his, nprR2, nprE18, A aprA3, epr::cat) have been described (See, Wong S. L, L.F. Wang and R. H. Doi (1988) "Cloning and nucleotide sequence of senN, a novel 'Bacillus natto' (B. subtilis) gene that regulates expression of extracellular protein genes." *J. Gen. Microbiol.* 134: 3269–3276; Kawamura and Doi, 1984, supra.). Plasmid papr contained the apr gene on a SmaI-PstI fragment (See, FIG. 7; the plasmid is described in Park, S.-S. et al, (1989) "*Bacillus subtilis* subtilisin gene (aprE) is expressed from a $\sigma^a$ ($\sigma^{43}$) promoter in vitro and in vivo." *J. Bacteriol.* 171 2657–2665). Plasmid pS1 containing the epr gene on a SphI-SalI fragment (FIG. 7) is a subclone obtained during the characterization of the 7.5 kb epr fragment obtained from the DB204 transformant described above. FIG. 7 depicts restriction maps and deletions of extracellular protease genes. The fragments of three cloned protease genes that have been used to construct the deletions are shown in FIG. 7. The fragments deleted are indicated by solid bars. Location of the promoters is shown by arrows. The direction of transcription is from left to right. Signal peptides are represented by stippled bars, pro-regions by hatched bars, and mature parts of the protease open reading frames by open bars. Plasmid pNPRsubH1 containing most of npr (Yang et al., 1984, supra) was obtained from D. Henner. Plasmids pUBHR and pUB18 are pUB110 derivatives (Wong et al., 1988, Supra.).

DNA manipulation and transformation

Plasmid DNA isolation and manipulations, chromosomal *B. Subtilis* DNA extraction, M13 cloning and transformation of competent *B. subtilis* cells followed procedures as set forth in (Maniatis et al., supra; Marmur, supra; Messing, supra; Contente and Dubnau, supra.). DNA sequencing was done by the chain terminating method (Sanger et al., 1977, supra.). Southern blot analysis was performed as described in Kawamura and Doi, 1984, supra.

Determination of protease activity

Protease activity was determined using Hide powder azure (Sigma) as substrate according to Wang and Doi, 1987, supra, as described above. To visualize protease action *B. subtilis* culture supernatants were concentrated with 80% ammonium sulfate, dissolved in 10 mM Tris, pH 7.8, 5 mM $CaCl_2$ and spotted on agar plates containing 1% skim milk or 1% gelatine respectively. The plates were incubated for 10–20 hours at 37° C. and clearing of the plates could be seen directly (skim milk) or after staining with Coomassie-blue (gelatine).

RESULTS

Inactivation of epr in B, subtilis DB104

The *B. subtilis* strain DB802 was obtained by introducing into DB104 the epr gene which had been insertionally inactivated by the cat gene of pUB112. (See discussion above under the section entitled "Mapping of the cloned gene.") The resulting strain, DB802, produced reduced levels of extracellular protease activity compared to the parental strain. As expected, the residual activity was inhibited by PMSF, because Roitsch and Hageman had reported the presence of another serine protease designated bacillopeptidase F, probably the most abundant remaining protease in the triple mutant strain. (See, Roitsch, C. A. and J. M. Hageman (1983) "Bacillopeptidase F: two forms of a glycoprotein serine protease from *Bacillus subtilis* 168." *J. Bacteriol* 155: 145–152.) However, as previously stated, (See discussion above under section entitled "Characterization of the protease.") a large portion of the remaining proteolytic activity was also inhibited by EDTA. DB104 contained a mutation in npr, nprE18, preventing the expression of neutral protease, a metalloenzyme (See, Uehara H., K. Yamane, B. Maruo (1979) "Thermosensitive extracellular neutral proteases in *Bacillus subtilis* isolation characterization, and genetics." *J. Bacter.* 189:583–590. However, since the nprE18 lesion had not been defined at the molecular level, the mutant nprE18 allele of the neutral protease gene was cloned and characterized as follows:

Characterization of the nprE18 mutation

An attempt was made to locate the nprE18 mutation inside npr by trying to correct it with plasmid pNPRsubH1 that contained most of npr without the signal peptide and part of the pro-region on a HindIII fragment (Yang et al., 1984, supra.). No correction was observed and it was therefore concluded that the mutation would be located upstream of the HindIII site (FIG. 7). To clone that part of npr, the HindIII-pvUII fragment (FIG. 7) was moved into the polylinker region of pUBHR. The resulting plasmid, pWL254, was then used to clone the missing BglII-HindIII fragment (FIG. 7) to restore the whole npr gene.

Chromosomal DB2 DNA was digested with BglII and HindIII and fractionated on an agarose gel. Isolated 1–1.5 kb fragments were ligated with pWL254 cut with BamHI and HindIII and transformed to DB104. A transformant producing a large halo on TBAB skim milk plates was found to contain pWL267 with the expected BglII-HindIII fragment (FIG. 7). The identity of npr on that fragment was confirmed by sequencing the StuI-HindIII fragment (FIG. 7) that had been moved to M13mp18/19.

With the wild type copy of npr on pWL267 DB104 was transformed and the transformants were screened for a reduced halo on skim milk plates. This phenotype would be the result of a gene conversion event during transformation (See, Iglesias A, and T. Trautner (1983) "Plasmid deficient *Bacillus subtilis*: Symmetry of gene conversion in transformation with a hybrid plasmid containing chromosomal DNA." *Mol. Gen. Genet.* 189:73–76.) when the nprE18 mutation from the chromosome is introduced by mismatch repair into the wild type npr on the plasmid. Transformants with an inactivated npr appeared at a frequency of 2% in this experiment. From two of the transformants with a reduced halo the plasmids, pWL276 and pWL277, were isolated and their restriction maps were compared with pWL267. No change in the restriction pattern could be detected. Replacing the StuI-HindIII fragment of pWL267 with the StuI-HindIII fragments of pWL276/277 inactivated npr on pWL267. The nprE18 mutation must therefore be located on that fragment.

Sequence comparison of the mutant fragments with the wild type revealed in both cases two point mutations. It was twice a C to T transition changing CAG, the codon for Gln at position 26 to the stop codon TAG, and AAC, the codon for Asn at position 44, to AAT. The nonsense mutation at amino acid position 26 was determined to be responsible for the nprE18 phenotype, since the second mutation could still be translated into protein and would not alter the amino acid at that position. Although protease expression directed by the nprE18 plasmids pWL276/277 was greatly reduced compared to the expression by the wild type npr plasmid pWL267, it was still well above the background protease production without any cloned npr allele. This was the result of some leakiness of the TAG nonsense mutation which could also explain the residual, low level expression of neutral protease in DB104.

Construction of the triple extracellular protease deficient strain

The triple protease deficient strain was constructed by introducing defined deletions into three genes for extracellular proteases. First, in order to prevent any low level expression of the genes a deletion in the respective gene was generated in vitro, which removed promoter, signal peptide and part of the pro-region. Secondly, the deleted copy of the gene was introduced into the *B. Subtilis* genome by gene conversion after transformation with a plasmid carrying the deletion. The inactivation of the target gene could be detected by the reduction of the halo size of some of the transformants on skim milk plates. Subsequently, transformants exhibiting a reduced halo size were cured of the deletion plasmids and the correct introduction of the deletions into the protease genes on the chromosome was confirmed by Southern blot analysis. In previously constructed mutants the applied internal deletions or insertions left the 5'-ends of the protease genes intact (Kawamura and Doi, 1984, Supra; Yang et al., 1984, Supra; Fahnestock C. A. and K. E. Fisher (1987) "Protease deficient *Bacillus subtilis* host strains for the production of staphylococcal protein A." *Appl. Environ, Microbiol.* 53: 379–389.) Depending on where the deletions or insertions were located, truncated preproproteins were produced which should be capable of entering the secretion pathway of the cells. One limiting step for overproduction of secreted proteins could be the availability of the secretcry apparatus. Total prevention of production of even truncated proteases could help to keep some secretcry capacity clear for the protein to be overproduced. Thus, the whole 5'-region of the protease open reading frames including the promoters were deleted.

Since more than 90% of the extracellular proteolytic activity of *B. subtilis* wild type is due to either neutral or alkaline protease, the first being more abundant than the latter, the order of inactivation was npr, apr and then epr. For the npr deletion the StuI-HindIII fragment (FIG. 7) was removed and the inactivated gene was integrated into DB2 yielding DB401. Into DB401 an apr deletion from EcoRI to HpaI (FIG. 7) was introduced. The double mutant, DB402, indeed produced less secreted protease activity than DB104 confirming that a residual level of neutral protease was being expressed in the nprE18 mutant. To inactivate the third Gene, epr, the HpaI-BamHI fragment (FIG. 7) was deleted and the deletion mutation was introduced to DB402. In the resulting strain, DB403, correct integration of all deletion variants was confirmed by Southern blot analysis and extracellular protease activity was tested and compared with that of the parental strains.

Although most of the protease activity is removed by deleting npr and apr a considerable further decrease is achieved by inactivation of epr (FIG. 8). FIG. 8 shows the extracellular protease expression of the *B. subtilis* mutants. (From left to right protease expression of *B. subtilis* wild type DB2 (trpC2), DB401 (trpC2, Δnpr), DB402 (and DB403 (trpC2, Δnpr, Δapr, Δepr) are shown. Lane A shows the cells on TBAB plates with 1% skim milk after 20 hours at 37° C. In B the same plate is shown after the cells have been washed off. In C, 10 ml of culture supernatants (in LB medium) harvested 3 hours after the onset of stationary phase were concentrated with 80% ammonium sulfate, dissolved in 10 mM Tris, pH 7.8., 5 mM $CaC_2$. 5 μl were spotted on agar plates containing 1% skim milk and incubated for 10 hours at 37° C. In D, 5 μl of the same culture supernatants were incubated for 10 hours at 37° C. on agar plates with 1% gelatine. Protease action was t, isualized by staining the plates with Coomassie-blue. The triple protease mutant strain of this invention, DB403, which grew and sporulated normally, produced about 1% of the extracellular proteolytic activity that is found in wild type culture supernatants. The residual activity could be almost completely inhibited by PMSF and is probably due to the presence of bacillopeptidase F, also a serine protease (Roitsch and Hagemann, 1983, supra.), but different from the one encoded by epr. The triple extracellular protease mutant strain DB403 should be a superior host for the production of heLerologous proteins in *B. subtilis*.

While the invention has been described in connection with certain specific embodiments thereof it should be realized that various modifications as may be apparent to one of skill in the art to which the invention pertains also fall within the scope of the invention as defined by the appended claims.

What is claimed is:

1. An isolated DNA molecule having a sequence coding for the *Bacillus subtilis* extracellular serine protease, Epr.

2. An isolated DNA molecule comprising a sequence coding for a serine protease polypeptide comprising the nucleotide sequence of FIG. 3 starting at nucleotide 1 and extending through to nucleotide 2398.

3. An isolated DNA molecule comprising a sequence of less than 2.4 kb coding for a serine protease polypeptide comprising the nucleotide sequence of FIG. 3 starting at nucleotide 439 and extending through to nucleotide 2398.

4. An isolated DNA molecule comprising a sequence of less than 2.4 kb coding for a serine protease polypeptide comprising the nucleotide sequence of FIG. 3 starting at nucleotide 461 and extending through to nucleotide 2398.

5. An isolated DNA molecule comprising a sequence of less than 2.4 kb coding for a serine protease polypeptide comprising the nucleotide sequence of FIG. 3 starting at nucleotide 770 and extending through to nucleotide 2398.

6. An isolated and purified DNA molecule encoding a polypeptide having the amino acid sequence of FIG. 3 starting at amino acid 1 and extending through to amino acid 645.

7. An isolated and purified DNA molecule encoding a polypeptide having the amino acid sequence of FIG. 3 starting at amino acid 104 and extending through to amino acid 645.

8. An isolated and purified DNA molecule having a sequence of less than 2.0 kb encoding a polypeptide having the amino acid sequence of FIG. 3 starting at amino acid 104 and extending through to amino acid 404.

9. The DNA molecule of claim 5 operably linked to control sequences for expressing said DNA in a compatible host.

10. A *Bacillus* host transformed, transfected, infected, injected or electroporated with the DNA of claim 9 or the RNA resulting from the transcription of said DNA.

11. The DNA molecule of claim 2 operably linked to control sequences for expressing said DNA in a compatible host.

12. A *Bacillus* host transformed, transfected, infected, injected or electroporated with the DNA of claim 11 or the RNA resulting from the transcription of said DNA.

13. The DNA molecule of claim 8 operably linked to control sequences for expressing said DNA in a compatible host.

14. A *Bacillus* host transformed, transfected, infected, injected or electroporated with the DNA of claim 13 or the RNA resulting from the transcription of said DNA.

15. The plasmid pHS1. ATCC accession number 75306.

16. The plasmid pHC1, ATCC accession number 75307.

17. A biologically pure culture of a mutant strain of *Bacillus subtilis* that is Epr protease deficient as a result of deletion of the epr gene or a portion of said gene such that active Epr protease is not produced.

18. A biologically pure culture of a mutant strain of *Bacillus subtilis* wherein the epr promoter and the structural gene including the signal peptide and a portion of the pro-region having the nucleotide sequence of FIG. 3 starting at nucleotide 1 and extending through to nucleotide 700 are deleted.

19. A biologically pure culture of a triple mutant strain of *Bacillus subtilis* that is Epr, Apr and Npr protease deficient as a result of deletion of the epr. apr and npr genes or a portion of said genes such that active Epr, Apr and Npr proteases are not produced.

20. A genetically engineered deletion mutant strain according to claim 26 wherein said strain produces less than 1% of the extracellular protease activity of wild type *Bacillus subtilis* cells that have the structural genes coding for extracellular neutral protease, extracellular alkaline serine protease and extracellular serine protease.

21. A biologically pure culture of a deletion mutant strain of *Bacillus subtilis* having genetically engineered deletions in the structural genes that code for extracellular neutral protease, extracellular alkaline protease, and extracellular serine protease wherein said strain has the identifying Npr, Apr and Epr protease deficient characteristics of *Bacillus subtilis* mutant strain DB403 (nprE, aprE, epr), ATCC accession number 55408.

22. The *Bacillus subtilis* mutant strain DB403, ATCC accession number 55408.

23. An isolated DNA molecule comprising a sequence coding for a serine protease polypeptide comprising the nucleotide sequence of FIG. 3 starting at nucleotide 1 and extending through to nucleotide 1672.

24. An isolated DNA molecule comprising a sequence of less than 2.4 kb coding for a serine protease polypeptide comprising the nucleotide sequence of FIG. 3 starting at nucleotide 439 and extending through to nucleotide 1672.

25. An isolated DNA molecule comprising a sequence of less than 2.4 kb coding for a serine protease polypeptide comprising the nucleotide sequence of FIG. 3 starting at nucleotide 461 and extending through to nucleotide 1672.

26. An isolated DNA molecule comprising a sequence of less than 2.4 kb coding for a serine protease polypeptide comprising the nucleotide sequence of FIG. 3 starting at nucleotide 539 and extending through to nucleotide 1672.

27. An isolated DNA molecule comprising a sequence of less than 2.4 kb coding for a serine protease polypeptide comprising the nucleotide sequence of FIG. 3 starting at nucleotide 770 and extending through to nucleotide 1672.

28. A biologically pure culture of a deletion mutant strain of *Bacillus subtilis* that does not produce the extracellular serine protease Epr and does not contain DNA having the nucleotide sequence of FIG. 3 starting at nucleotide 1 and extending through to nucleotide 2398.

29. A biologically pure culture of a deletion mutant strain of *Bacillus subtilis* that does not produce the extracellular serine protease Epr and does not contain DNA having the nucleotide sequence of FIG. 3 starting at nucleotide 1553 and extending through to nucleotide 1672.

30. A biologically pure culture of a deletion mutant strain of *Bacillus subtilis* that does not produce the extracellular serine protease Epr and does not contain DNA having the nucleotide sequence of FIG. 3 starting at nucleotide 1 and extending up to and including nucleotide 1672.

31. A biologically pure culture of *Bacillus subtilis* that does not produce functional Epr serine protease as a result of a deletion in the epr gene.

32. A biologically pure culture of *Bacillus subtilis* that does not produce functional Epr, Apr and Npr serine proteases as a result of deletions in the epr, apr and npr genes.

33. A biologically pure culture of a deletion mutant strain of *Bacillus subtilis* wherein the nucleotide sequence coded on the StuI-HindIII fragment of npr, the nucleotide sequence coded on the EcoRI-HpaI fragment of apr and the nucleotide sequence coded on the HpaI-BamHI fragment of epr are deleted.

* * * * *

UNITED STATES PATENT AND TRADEMARK OFFICE
CERTIFICATE OF CORRECTION

PATENT NO. : 5,585,253

DATED : December 17, 1996

INVENTOR(S) : DOI et al.

It is certified that error appears in the above-indentified patent and that said Letters Patent is hereby corrected as shown below:

Title page, item [54] Col.1, line 3 delete "AN SERINE" and insert therefor --AND SERINE--.

At column 2, line 66, delete "A" and insert therefor --Δ--.

At column 3, line 11, delete "iSpl::cat)" and insert therefor --ispl::cat)--.

At column 3, line 17, delete "suprA" and insert therefor --supra--.

At column 3, line 50, delete "SaU3AI" and insert therefor Sau3AI--.

At column 4, line 24, delete "41904195)" and insert therefor --4190-4195)--.

At column 4, line 39, delete "-leu-" and insert therefor ---phe---.

At column 5, line 23, delete "Of" and insert therefor --of--.

At column 5, line 31, delete HinQII" and insert therefor --HincII--.

At column 6, line 63, delete "yon Heijne" and insert therefor --von Heijne--.

At column 7, line 42, delete "pRB274'laC" and insert therefor --pRB274'lac--.

UNITED STATES PATENT AND TRADEMARK OFFICE
CERTIFICATE OF CORRECTION

PATENT NO. : 5,585,253

DATED : December 17, 1996

INVENTOR(S) : DOI et al.

It is certified that error appears in the above-indentified patent and that said Letters Patent is hereby corrected as shown below:

At column 7, line 62, delete "place" and insert therefor --placE--.

At column 7, line 63, delete "pRB274'laC" and insert therefor --pRB274'lac--.

At column 9, line 65, delete "p Construction" and insert new paragraphing followed by --Construction--.

At column 10, line 2, delete "A apr" and insert therefor --$\Delta$ apr--.

At column 10, line 3, delete "A apr" and insert therefor --$\Delta$ apr--.

At column 11, line 19, delete "-pvUII" and insert therefor --PvuII--.

At column 12, line 28, delete "seretcry" and insert therefor --secretory--.

At column 12, line 30, delete "seretcry" and insert therefor --secretory--.

At column 12, line 55, delete "DB402" and insert therefor --DB402 (trpC2, $\Delta$ npr $\Delta$ apr)--.

At column 12, line 62, delete "CaC$_2$" and insert therefor --CaCl$_2$--.

At column 12, line 66, delete "t,isualized" and insert therefor --visualized--.

UNITED STATES PATENT AND TRADEMARK OFFICE
CERTIFICATE OF CORRECTION

PATENT NO. : 5,585,253  Page 3 of 3
DATED : December 17, 1996
INVENTOR(S) : DOI et al.

It is certified that error appears in the above-indentified patent and that said Letters Patent is hereby corrected as shown below:

At column 13, line 10, delete "heLerologous" and insert therefor --heterologous--.

At column 14, claim 19, line 13 reads "epr." and insert therefor --epr,--.

At column 14, claim 20, line 18, delete "claim 26", and insert therefor --claim 19--.

Signed and Sealed this

Third Day of June, 1997

Attest:

BRUCE LEHMAN

Attesting Officer

Commissioner of Patents and Trademarks